(12) United States Patent
Pfleger et al.

(10) Patent No.: US 7,812,161 B2
(45) Date of Patent: Oct. 12, 2010

(54) SYNTHESIS OF GLYT-1 INHIBITORS

(75) Inventors: Christophe Pfleger, Riedisheim (FR); Pius Waldmeier, Wegenstetten (CH); Shaoning Wang, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 312 days.

(21) Appl. No.: 12/038,006

(22) Filed: Feb. 27, 2008

(65) Prior Publication Data
US 2008/0221327 A1 Sep. 11, 2008

(30) Foreign Application Priority Data
Mar. 5, 2007 (EP) .................... 07103485

(51) Int. Cl.
*C07D 213/75* (2006.01)
(52) U.S. Cl. .................... 544/360; 514/253.01
(58) Field of Classification Search .......... None
See application file for complete search history.

(56) References Cited

U.S. PATENT DOCUMENTS

| 3,992,441 | A | * | 11/1976 | Helland | 562/430 |
| 4,971,969 | A | | 11/1990 | Carlier | |
| 2002/0147337 | A1 | | 10/2002 | Wollmann et al. | |
| 2005/0209241 | A1 | * | 9/2005 | Jolidon et al. | 514/252.14 |
| 2006/0149062 | A1 | | 7/2006 | Jolidon et al. | |

FOREIGN PATENT DOCUMENTS

| EP | 0104715 | 4/1984 |
| EP | 0594027 | 4/1994 |
| WO | WO 99/54284 | 10/1999 |
| WO | WO 02/072538 | 9/2002 |
| WO | WO 2004/046124 | 6/2004 |
| WO | WO 2005/014563 | 2/2005 |
| WO | WO 2006/061135 | 6/2006 |
| WO | WO 2006/072436 | 7/2006 |
| WO | WO 2007/006650 | 1/2007 |

OTHER PUBLICATIONS

Armer et al., Exp. Opin. Ther. Patents, vol. 11(4) pp. 563-572 (2001).
Pralong et al., Prog. Neurobiol. vol. 67, pp. 173-202 (2002).
Carlsson M. L., J. Neural. Trans. vol. 105, pp. 525-535 (1998).
Lewis, et al., Neuron. vol. 28, pp. 325-333 (2000).
Vandenberg et al., Exp. Opin. Ther. Targets vol. 5(4) pp. 507-518 (2001).
Nakazato et al., Exp. Opin. Ther. Patents vol. 10(1) pp. 75-98 (2000).
Sharma, et al., J. Psychiatry, vol. 174, Suppl. 28, pp. 44-51 (1999).

* cited by examiner

*Primary Examiner*—Emily Bernhardt
(74) *Attorney, Agent, or Firm*—George W. Johnston; Patricia S. Rocha-Tramaloni; Kimberly J. Prior

(57) ABSTRACT

The present invention relates to a process for preparation of a compound of formula I

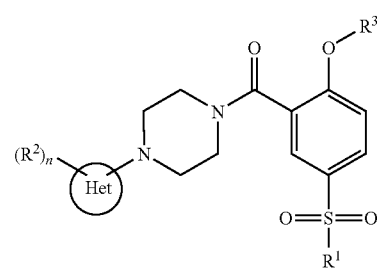

wherein
Het, $R^1$, $R^2$, $R^3$, and n are as defined herein and pharmaceutically acceptable acid addition salts thereof, which comprises reacting a compound of formula 21 with a compound of formula 8 to obtain a compound of formula 11 and coupling the compound of formula 11 in the presence of a coupling reagent or the corresponding acid halogenide with a compound of formula 15 to obtain a compound of formula I.

6 Claims, No Drawings

SYNTHESIS OF GLYT-1 INHIBITORS

PRIORITY TO RELATED APPLICATION(S)

This application claims the benefit of European Patent Application No. 07103485.4, filed Mar. 5, 2007, which is hereby incorporated by reference in its entirety.

BACKGROUND OF THE INVENTION

Glycine transporters inhibitors are suitable for the treatment of neurological and neuropsychiatric disorders. The majority of diseases states implicated are psychoses, schizophrenia (Armer R E and Miller D J, *Exp. Opin. Ther. Patents*, 11 (4): 563-572, 2001), psychotic mood disorders such as severe major depressive disorder, mood disorders associated with psychotic disorders such as acute mania or depression, associated with bipolar disorders and mood disorders, associated with schizophrenia, (Pralong E T et al., *Prog. Neurobiol.*, 67: 173-202, 2002), autistic disorders (Carlsson M L, *J. Neural Trans.*, 105: 525-535, 1998), cognitive disorders such as dementias, including age related dementia and senile dementia of the Alzheimer type, memory disorders in a mammal, including a human, attention deficit disorders and pain (Armer R E and Miller D J, *Exp. Opin. Ther. Patents*, 11 (4): 563-572, 2001).

The most preferred indication for compounds of formula I is schizophrenia.

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron*, 28:325-33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets*, 5(4): 507-518, 2001; Nakazato A and Okuyama S, et al., *Exp. Opin. Ther. Patents*, 10(1): 75-98, 2000). This pharmacological approach poorly address negative and cognitive symptoms which are the best predictors of functional outcome (Sharma T., *Br. J. Psychiatry*, 174(suppl. 28): 44-51, 1999).

The compounds of formula I are known compounds, described in WO 2005/014563.

The compounds, described therein, have been prepared for example in accordance with the following general scheme 1:

Scheme I

Compounds of general formula I have been prepared by reacting piperazine derivatives of formula 15 with a corresponding acid of formula 11 in the presence of an activating agent like TBTU (2-(1H-benzotriazole-1-yl)-1,1,3,3-tetramethyluroniumtetrafluoroborate). Piperazine derivatives of formula 15 have been prepared by heating of the corresponding N-protected piperazine 13 with HetX 12 in the presence of a base followed by cleavage of the protective group. The protective group was typically tert-butoxycarbonyl (Boc).

More specifically, a compound of formula I could be prepared as described in Scheme I in a 12 step synthesis.

The synthesis of the piperazine building block 15 started from a compound of formula 12, for example from 2,3-dichloro-5-trifluoromethyl-pyridine or from the expensive compound 2-Cl, 3-F, 5-trifluoromethyl-pyridine via halogen exchange to 14. Nucleophilic substitution with expensive Boc-piperazine 13 and subsequent Boc-deprotection yielded the piperazine derivative 15 in about 23 to 30%.

The main drawbacks of the above shown synthesis with regard to scalability were a) the handling of chlorosulfuric acid for the preparation of 4,
b) the instability of 4,
c) the low overall yield to 7,
d) the chiral HPLC separation of 10,
e) the expensive and low yielding synthesis of 14,
f) the very difficult purification of 14,
g) the expensive Boc-piperazine 13 and
h) the chromatographic purification of the building block 15.

SUMMARY OF THE INVENTION

The present invention provides a new, short and efficient scalable synthesis of Glyt-1 inhibitors of formula I, especially for the specific compound [4-(3-fluoro-5-trifluoromethyl-pyridin-2-yl)-piperazin-1-yl]-[5-methanesulfonyl-2-(S)-(2,2,2-trifluoro-1-methyl-ethoxy)-phenyl]-methanone with a cheap source and a cheap and practicable synthesis of the starting materials.

In particular, the present invention provides a new scalable synthesis of compounds of the general formula I

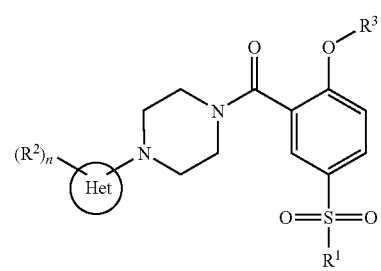

wherein
Het is a 6-membered heteroaryl group, containing one, two or three nitrogen atoms;
$R^1$ is $(C_1$-$C_6)$-alkyl, $(C_3$-$C_6)$-cycloalkyl, $NR^4R^5$ or $(C_1$-$C_6)$-alkyl substituted by halogen;
$R^2$ is hydroxy, halogen, $NO_2$, CN, $(C_1$-$C_6)$-alkyl, $(C_3$-$C_6)$-cycloalkyl, $(C_1$-$C_6)$-alkyl substituted by halogen, $(C_1$-$C_6)$-alkyl substituted by hydroxy, $(CH_2)_o$—$(C_1$-$C_6)$-alkoxy, $(C_1$-$C_6)$-alkoxy substituted by halogen, $NR^4R^5$, $C(O)R^6$ or $SO_2R^7$;
$R^3$ is $(C_1$-$C_6)$-alkyl, $(C_3$-$C_6)$-cycloalkyl or $(C_1$-$C_6)$-alkyl substituted by halogen;
$R^4$ and $R^5$ are each independently hydrogen or $(C_1$-$C_6)$-alkyl;
$R^6$ is hydrogen, $(C_1$-$C_6)$-alkyl, $(C_1$-$C_6)$-alkoxy or $NR^4R^5$;
$R^7$ is $(C_1$-$C_6)$-alkyl, $(C_1$-$C_6)$-alkyl optionally substituted by halogen, $(CH_2)_o$—$(C_3$-$C_6)$-cycloalkyl, $(CH_2)_o$—$(C_3$-$C_6)$-alkoxy or $NR^4R^5$;
n is 1, 2 or 3;
o is 0, 1 or 2;

and to pharmaceutically acceptable acid addition salts thereof.

The most preferred compound prepared by the new scalable synthesis is the compound of formula

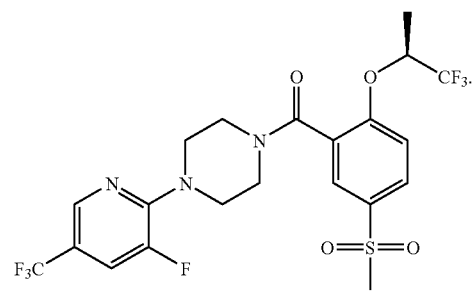

(S)-I-1

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As defined in formula I, the term "halogen" denotes chlorine, iodine, fluorine and bromine.

The term "alkyl" denotes a branched or straight carbon chain containing 1 to 6 carbon atoms.

The term "alkoxy" denotes a group wherein the alkyl residue is as defined above, and which is attached via an oxygen atom.

The term "6-membered heteroaryl containing one, two or three nitrogen atoms" denotes a monovalent aromatic radical, for example pyridyl, pyrazinyl, pyrimidinyl, pyridazinyl or 1,3,5-triazinyl.

The term "alkoxy, substituted by halogen" denotes an alkoxy residue as defined above wherein at least one hydrogen atom is replaced by halogen.

The term "alkyl substituted by halogen" denotes an alkyl residue as defined above wherein at least one hydrogen atom is replaced by halogen, for example the following groups: $CF_3$, $CHF_2$, $CH_2F$, $CH_2CF_3$, $CH_2CHF_2$, $CH_2CH_2F$, $CH_2CH_2CF_3$, $CH_2CH_2CH_2CF_3$, $CH_2CF_2CF_3$, $CH_2CF_2CHF_2$, $CF_2CHFCF_3$, $C(CH_3)_2CF_3$, $CH(CH_3)CF_3$ or $CH(CH_2F)CH_2F$.

The term "alkyl, substituted by hydroxy" denotes an alkyl residue as defined above wherein at least one hydrogen atom is replaced by a hydroxy group, for example $CH(OH)CH_3$, $CH_2CH(OH)CH_3$, $CH_2CH(CH_3)CH_2OH$, $(CH_2)_2OH$, $(CH_2)_3OH$ or $CH_2C[(CH_3)]_2$—$CH_2OH$.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

The present invention provides a new and efficient scalable 5 steps synthesis to prepare compounds of general formula I, which are good inhibitors of the glycine transporter 1 (GlyT-1) and which are selective to glycine transporter 2 (GlyT-2) inhibitors.

The problems encountered with Scheme 1 can be overcome by the instant invention, as described in schemes 2 and 3. Racemic compounds of formula I can be prepared in accordance with scheme 2:

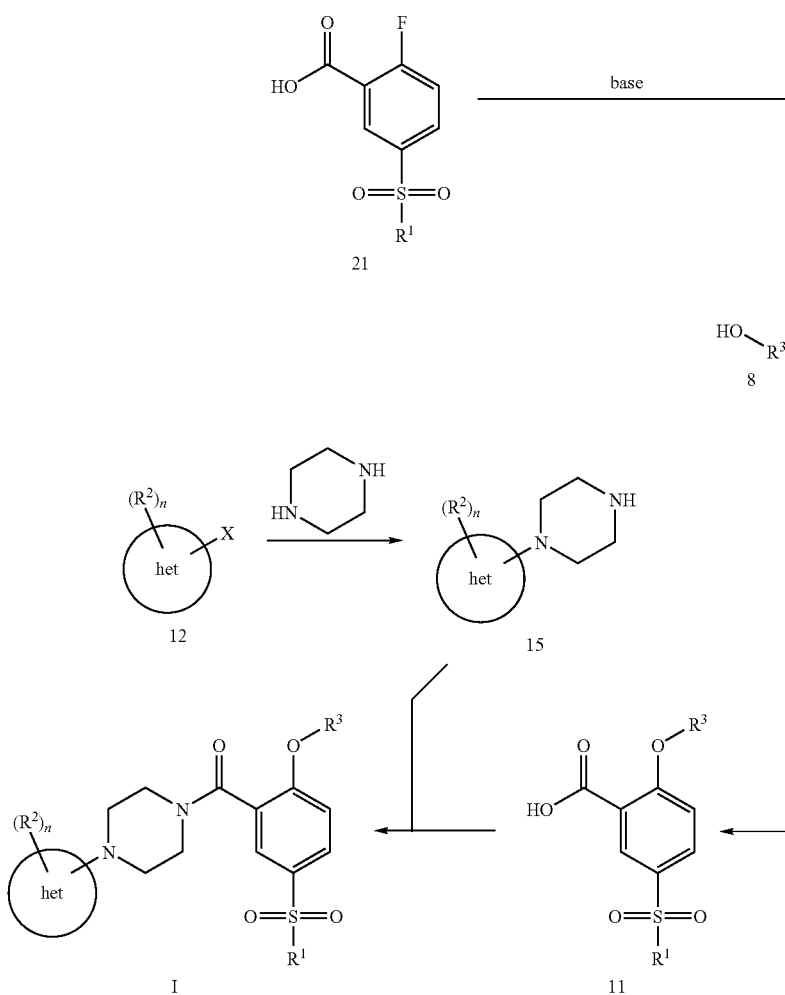

wherein X is a leaving group such as halogen (F, Cl, Br, I, mesylate, triflate or tosylate), $R^1$, $R^2$, het and n are as described above and $R^3$ is ($C_1$-$C_6$)-alkyl or ($C_1$-$C_6$)-alkyl substituted by halogen.

The corresponding S-enantiomers may be prepared according to scheme 3.

two steps from a compound of formula 12 or 12-1, such as dichloro-trifluoromethyl-pyridine (12-1). The reaction of 12-1 with CsF and $K_2CO_3$ in NMP give the corresponding difluoro trifluoromethylpyridine (12-2), which after reaction with piperazine lead to 15 or 15-1. The coupling of 15 or 15-1 with the corresponding acid chloride of 11, rac-11 or (S)-11-1

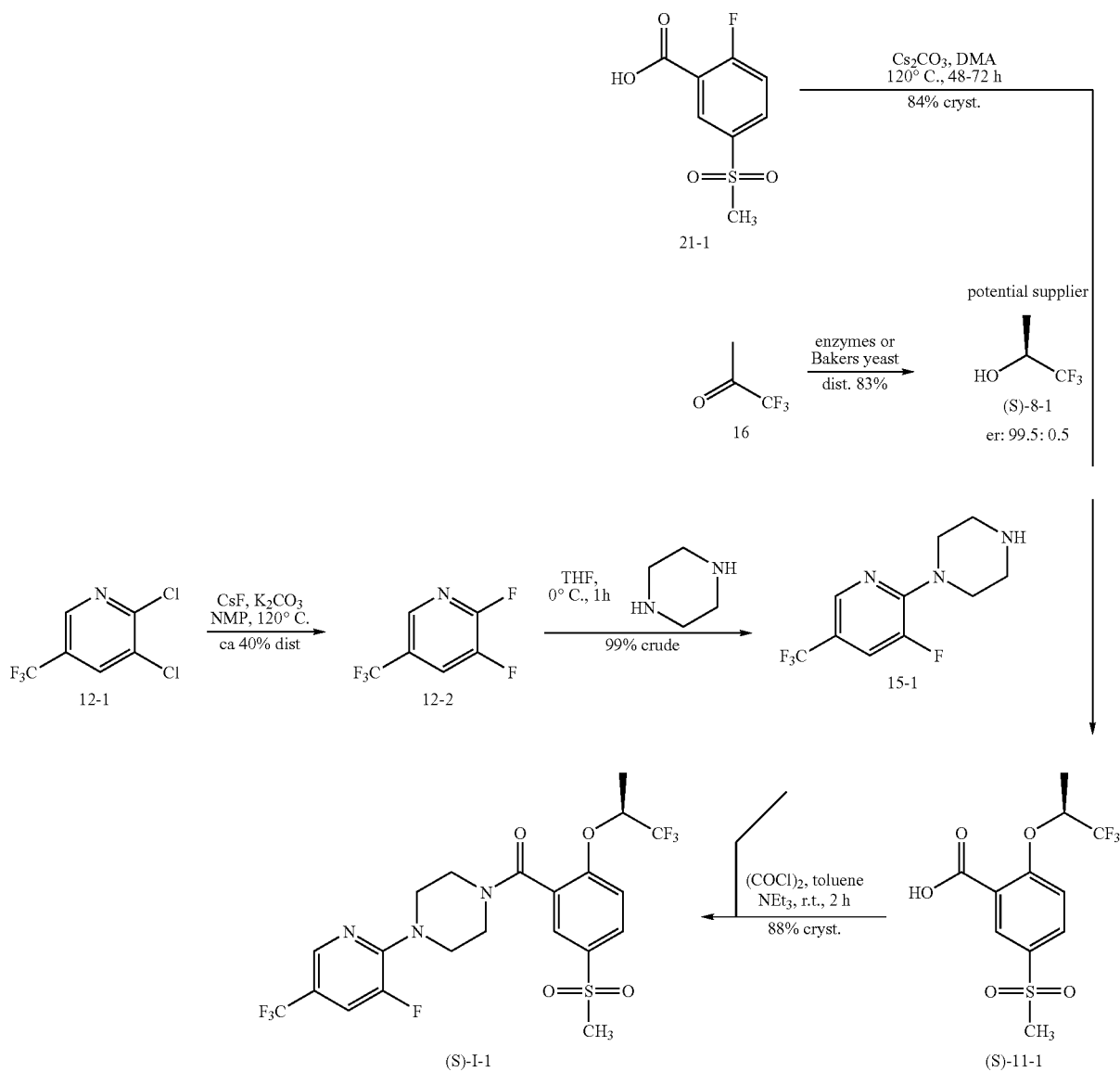

provides after crystallization the final compound I, rac-I or (S)-I-1 in ca. 74% overall yield.

This new process is described below in more detail:

1. Asymmetric Reduction of Trifluoroacetone (16)

a) With Baker's Yeast

Although (S)-8-1 was prepared successfully by enzymatic racemate resolution, development of the asymmetric reduction of 16 with Baker's yeast was continued to decrease the process cost. The goal was also to increase the enantiomeric A new, short and efficient scalable 5 (2+2+1) steps synthesis to the Glyt-1 inhibitor of formula I has been established by substituting the non-scalable known synthesis. The synthesis starts with the transformation of the fluoro-methanesulfonyl-benzoic acid 21 or 21-1 to the benzoic acid derivative 11, rac 11 or (S)-11-1 applying $HOR^3$ 8 or trifluoro-isopropanol (S)-8-1. (S)-8-1 is produced via the asymmetric reduction of trifluoroacetone (16) with Baker's yeast in 83% yield after distillation, or via asymmetric reduction with Ru-catalysts. The piperazine building block 15 or 15-1 is synthesized in purity of (S)-8-1 by optimization of the yeast-catalyzed biotransformation. Baker's yeast purchased from Klipfel AG was chosen (out of approx. 60 yeasts tested) as biocatalyst for reasons of cost and selectivity. A heat pre-treatment of the yeast at ca. 50° C. for 2 h increased the ee from 96 to >99%. Parameter optimization resulted in a process on the 10 l scale with a substrate concentration of 3% (w/v) and with biotransformation yields of ca. 83 to 96% after 5 to 6 days. The main by-product formed during the heat treatment of the yeast followed by the above described biotransformation was ethanol. A product isolation process was developed based solely on distillation and rectification. Highly purified (S)-trifluoro-isopropanol (S)-8-1 (<0.1% ethanol) was obtained as an azeotrope with 5% water. After up-scaling the process to the 800 l scale 21.8 kg (83% isolated yield) of (S)-trifluoro-isopropanol (S)-8-1, (er=99.7:0.3) were produced.

In addition to the microbial reduction, the technical potential of isolated alcohol dehydrogenases (ADH) was also investigated. It was feasible to produce g-amounts of both the S- and R-enantiomer in high enantiomeric excess. The required (S)-8-1 was reproducibly obtained with an er>99.5:0.5. However, as the best ADH from *Sacharomyces cerivisiae* is sold solely as a diagnostic enzyme (Roche Penzberg) the enzyme was rated far too expensive.

b) With Catalysts

Chemically and enantiomerically pure (S)-1,1,1-trifluoro-2-propanol (S)-8-1 may also be prepared by an asymmetric hydrogenation of 1,1,1-trifluoroacetone with ruthenium phosphine complexes in the absence of a base and an additive.

2. Synthesis of Starting Material 21 or 21-1

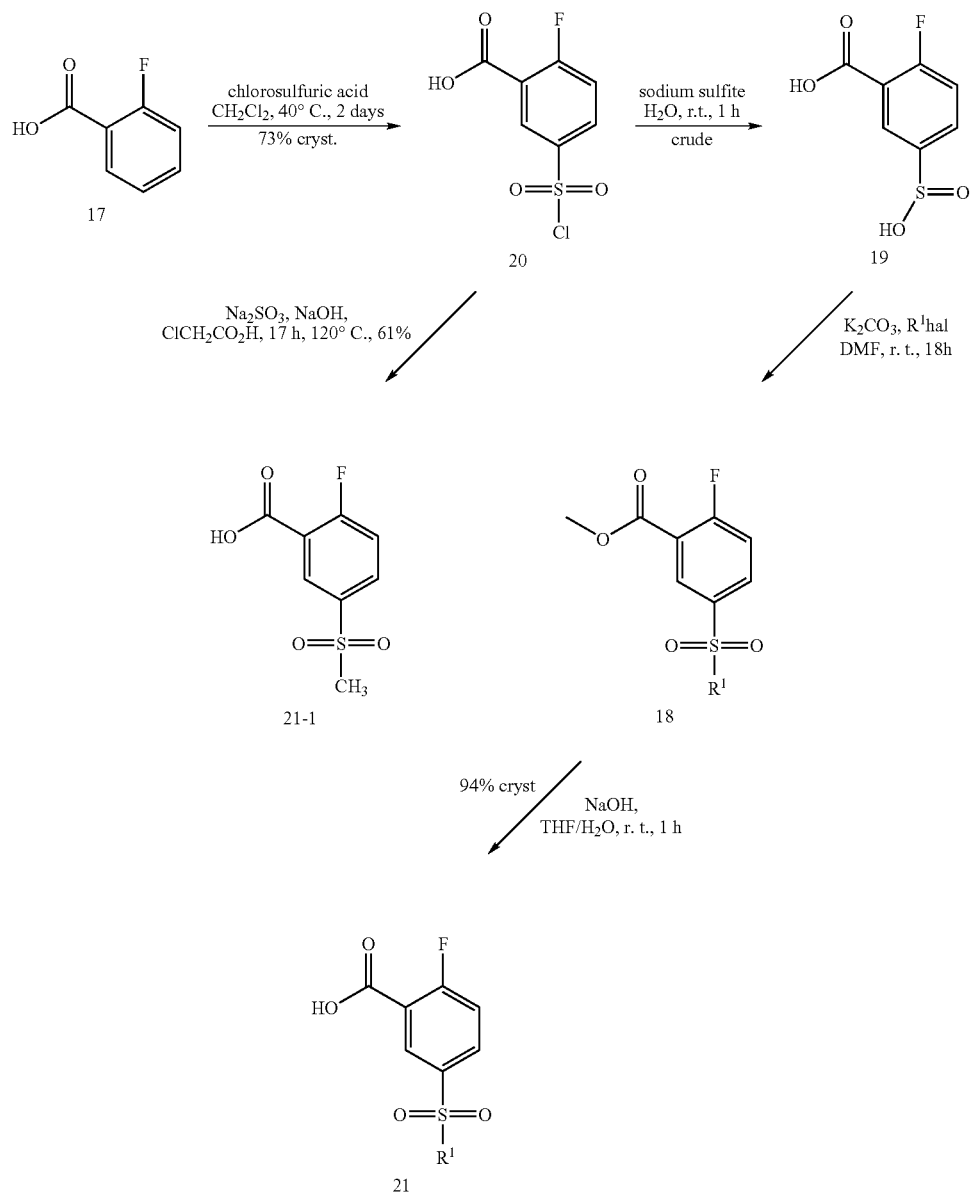

The intensive trouble-shooting of the 4-step sequence from 2-fluorobenzoic acid (17) to 21 succeeded in an overall yield improvement from 17 to 50%. The main enhancement was achieved by optimizing the reaction conditions to 19 with sodium sulfite followed by the alkylation reaction with $R^1$hal (hal=I, Cl, Br) yielding 21 after saponification and crystallization. In a non-optimized reaction a one-pot procedure from 20 to 21-1 was demonstrated applying sodium sulfite in NaOH 32% followed by the treatment of $ClCH_2CO_2H$ yielding 21-1 in 61% analogue to WO02/07238.

3. Improved Synthesis of (S)-11-1

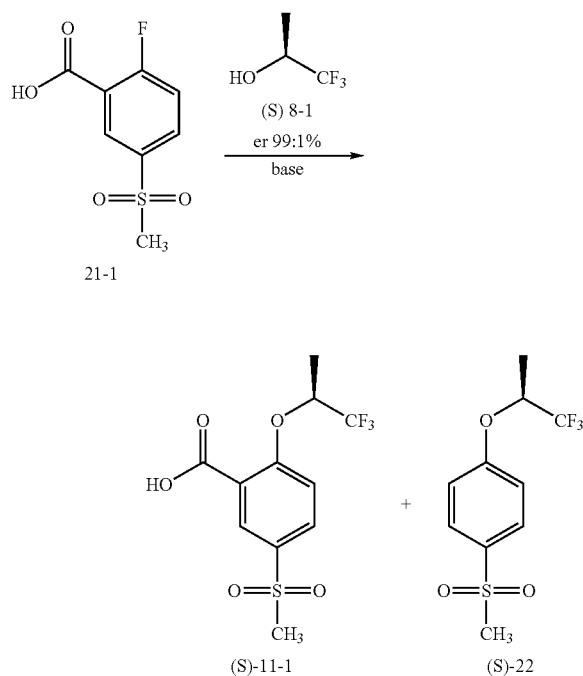

Various conditions were tested to improve the original non-technical condition during the conversion of 21-1 to (S)-11-1 applying $K_2CO_3$ (3 eq.) and (S)-trifluoro-isopropanol (5 eq.) in DMA, microwave irradiation at 150° C. for 2 h yielding ca. 35% to 71%. Due to the volatility of the (S)-trifluoro-isopropanol the reaction was performed in a closed vessel. Replacing $K_2CO_3$ (3 eq., 40% starting material left) by $Cs_2CO_3$ (3 eq.) the reaction was completed within 3 h at 150° C. without irradiation. Lower reaction temperature and less $Cs_2CO_3$ led to longer reaction time (up to 20 h). Our focus was to reduce the amount of the expensive (S)-trifluoro-isopropanol, resulting in the reduction of (S)-8-1 from 5 eq. to 1.25 eq. The conditions applied $Cs_2CO_3$ (1.9 eq.) and (S)-trifluoro-isopropanol (1.4 eq.) in DMA at 120° C. (1.5 bar) for 72 h yielded after work-up white crystals of (S)-11-1 in 84-90%. Extended reaction time (90 h) at 150° C. and 5 bar led to the decarboxylated by-product (S)-22 (up to 30%), which was separated from the desired intermediate (S)-1-1 via basic extraction.

In detail, the reaction is performed with 1-5 eq. bases like $Na_2CO_3$, $K_2CO_3$, $Li_2CO_3$ or $Cs_2CO_3$, preferably 2-3 eq. $Cs_2CO_3$ in high boiling solvents like NMP or DMA preferably DMA at temperature e.g. in the range between 60° C. and the boiling point of the solvent, preferably between 100° C. and 150° C. for 1 to 90 h, preferably 24-48 h or with 1-5 eq. bases like NatOBu, LitOBu or KtOBu, preferably 1-1.5 eq. KtOBu in solvents e.g. like DMF or THF, preferably THF at temperature e.g. in the range between 0° C. and the boiling point of the solvent, preferably between 20° C. and 50° C. for 1 to 30 h, preferably 3-8 h.

4. Optimized Procedure to Difluoro Trifluoromethyl Pyridine (12-2)

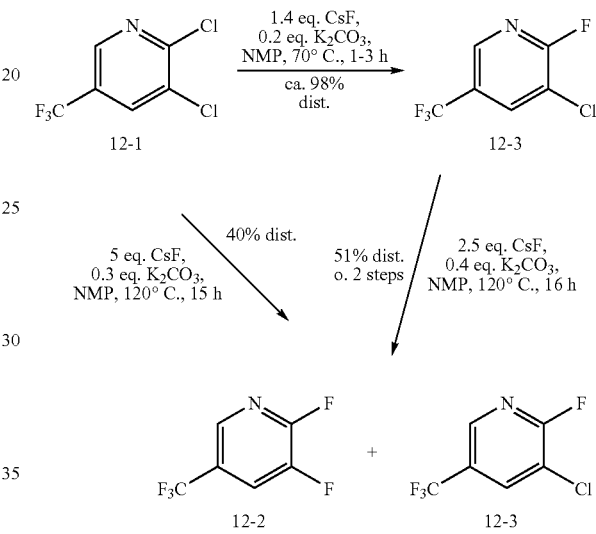

The synthesis of the 12-2 was elaborated starting from the corresponding dichloro compound 12-1 or from the very expensive chloro-fluoro compound 12-3. The reactivity of the chloro atom in the 2-position of 12-1 is significant higher compared with the chloro atom in the 3-position. Based on the known safety issue of DMSO in combination with bases like $K_2CO_3$ at high temperatures like 120° C., DMSO was substituted by N-methylpyrrolidinone (NMP). The heterogenic reaction is very water-sensitive. Traces of water led to longer reaction time and/or incomplete conversion. Longer reaction time (more than 17 h at 120° C.) or higher temperature led, due to the instability of the product 12-2, to several unknown by-products, ending up as a black tar in the reaction vessel. Therefore, it was necessary to work with water free solvent. A substantial amount of CsF was needed for this reaction. CsF is very hygroscopic and contaminated the reaction mixture with water. Therefore, to completely eliminate water from the reaction mixture, a defined amount of NMP was evaporated prior to the addition of dichloro compound 12-1 to the suspension of $K_2CO_3$ and CsF in NMP.

During scale-up it was difficult to control the reaction and to get pure, solvent free 12-2 out of the reaction mixture due to the small difference between the boiling points of 12-3 and 12-2. Under optimized distillation conditions, it was possible to obtain material at a ratio of 12-3 to 12-2 of about 0.3 to 99.7 containing DMSO.

5. Short Synthesis of the Piperazine Building Block 15

The crude 15 was directly coupled with 11, rac-11 or (S)-11-1 in the final step to API I, rac-I or (S)-I. Several coupling reagents like TBTU, HBTU, CDI and EDCI (in DMF, THF or $CH_2Cl_2$) were tested for this type of coupling,

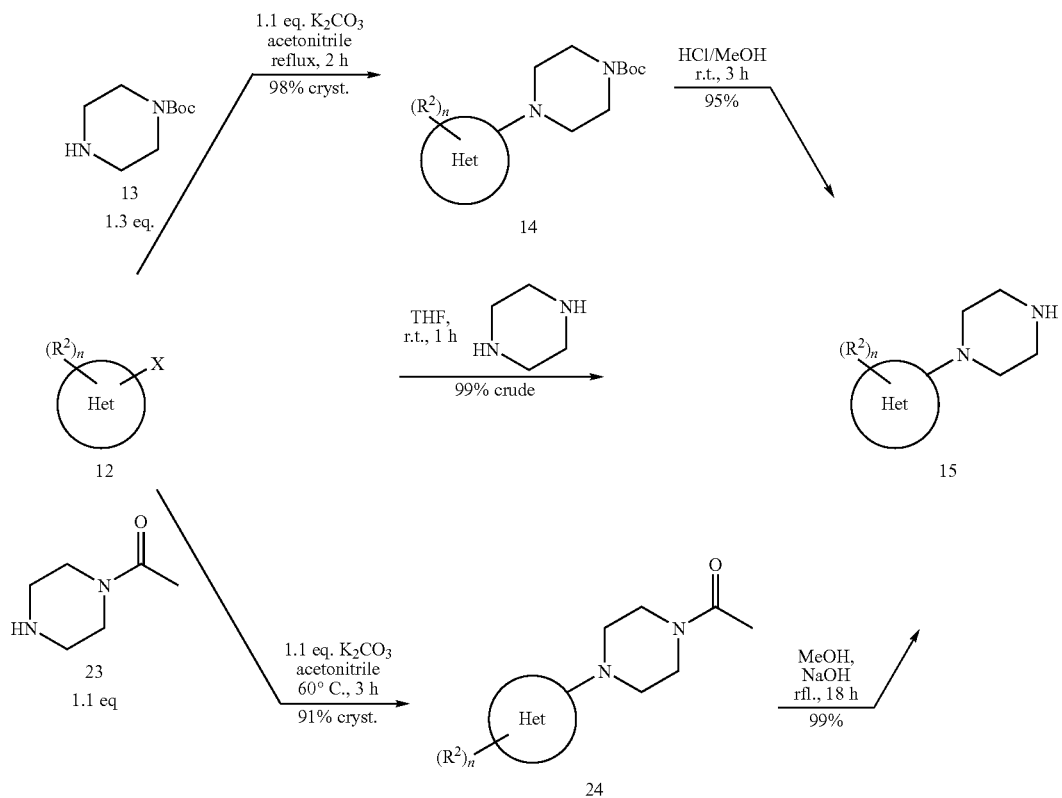

wherein X is a leaving group such as F, Cl, Br, I, mesylate, triflate or tosylate.

In usual manner, the piperazine building block 15 may be synthesized by applying 12, bases like $K_2CO_3$ 1-3 eq. preferably 1.5 eq. and the expensive Boc-piperazine 1-3 eq. preferably 1.1 eq. in solvents like e.g THF, toluene, acetonitrile preferably acetonitrile at temperature e.g. in the range between 0° C. and the boiling point of the solvent, preferably between 40° C. and 70° C. for 1 to 16 h, preferably 3 h. The subsequent Boc-deprotection under the conditions trifluoro acetic acid in $CH_2Cl_2$ at room temperature for 3 h and basic work-up yielded 15 in ca. 88% over two steps.

Furthermore, a modification of the Boc-deprotection procedure using HCl in MeOH at room temperature for 3 h provided the crystalline 15.HCl in 93% overall yield, which was directly used as HCl salt in the final coupling step. Due to its high price Boc-piperazine was substituted by the cheap acetyl piperazine yielding 24 in 91% after crystallization. N-acetyl deprotection using aq. NaOH in MeOH under reflux for 18 h led to 15 in 99% yield.

A one-step procedure applying cheap piperazine in solvents like e.g THF, toluene, acetonitrile preferably THF at temperature e.g. in the range between 0° C. and the boiling point of the solvent, preferably at room temperature for 1 to 16 h, preferably 1 h was finally developed yielding the crude 15 after aqueous work-up in quantitative yield.

whereby in all cases a chromatographic purification was needed to get pure final compound of formula I, rac-I or (S)-I in 35 to 78% yield. The coupling via the mixed anhydride applying ethyl chloroformate in $CH_2Cl_2$ yielded after crystallization the pure I, rac-I or (S)-I in 75 to 80%.

In accordance with the above described new process, the following advantage over the known procedure can be provided:

The synthesis was shortened from 12 to 5 steps.
The overall yield increased from ca. 7% to 74%.
A cheap source and a cheap and practicable synthesis of the starting materials 21, 15 and (S)-8-1 were identified.
The use of the expensive protected piperazine 13 has been avoided.
An efficient procedure was developed to synthesize the compound 15.
All chromatographic purifications were eliminated.

The following abbreviations have been used in the description and claims:

| TBTU | (2-(1H-benzotriazole-1-yl)-1,1,3,3-tetramethyluroniumtetra-fluoroborate) |
|---|---|
| NMP | N-methyl pyrrolidinone |
| DMF | N,N-dimethylformamide |

| | |
|---|---|
| TFA | trifluoroacetic acid |
| DMA | dimethylamine |
| THF | tetrahydrofuran |
| DMSO | methyl sulfoxide |
| CDI | 1,1'-carbonyldiimidazole |
| EDCI | 1-(3-dimethylaminopropyl)-3-ethylcarbodiimide |

EXAMPLE 1

5-Methanesulfonyl-2-(2,2,2-trifluoro-1-methyl-ethoxy)-Benzoic Acid ((S)-11-1)

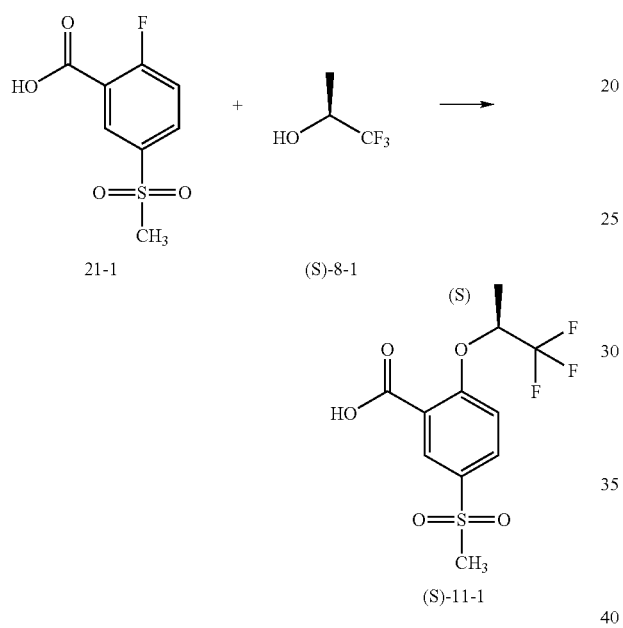

Equipment: 12 l autoclave

A colorless solution of 700.0 g 2-fluoro-5-methanesulfonyl-benzoic acid (21-1, 3.2 mol) in 7.7 l N,N-dimethyl-acetamide was treated with 1965.0 g cesium carbonate (6.0 mol) and 522.8 (S)-trifluoro-isopropanol (S)-8-1 (4.5 mol). The white reaction suspension was warmed to 120° C. and stirred under argon for 72 h (1.5 bar).

After cooling to 20° C. the white suspension was filtered, the filter cake was washed with 500 ml N,N-dimethyl-acetamide and the filtrate was evaporated. To the residue was added 9 l water and the solution was extracted 3 times with 7 l, in total with 21 l ethyl acetate. The aqueous phase was heated in the rotary evaporator to completely remove residual ethyl acetate from the water phase. The pH of the water phase was adjusted to 1.5 by addition of 600 ml HCl 37%, whereby the product precipitated. The suspension was stirred at room temperature for 1 h, filtered, the crystals were washed with 5 l water and dried under high vacuum for 24 h at 50° C. to yield 840.0 g (84.0%) of (S)-1-1 as white crystals.

HPLC analysis 99.6 area-% of (S)-11-1. er=99.2:0.8% (HPLC)

or:

Equipment: 500 ml double-jacket vessel equipped with a temperature probe, a mechanical stirrer, a cooler and an inert gas supply.

A colorless solution of 65.5 g 2-fluoro-5-methanesulfonyl-benzoic acid (21-1, 300 mmol) in 300 ml THF was treated at room temperature with 38.0 g (S)-trifluoro-isopropanol (S)-8-1 (330 mmol). The reaction mixture was treated within 1 h with a solution of 71.4 g KOtBu (630 mmol) in 300 ml THF (exothermic reaction). The light-yellow suspension was warmed to 50° C. within 1 h and stirred under argon for 2 h.

To the reaction mixture was added at 50° C. within 15 min 48 g formic acid. The solvent of the mixture was evaporated (50° C., 300-150 mbar). To the residue was added 40 ml EtOH, stirred for 5 min at 40° C. and treated within 5 min at 46-48° C. with 150 ml water, stirred for 5 min and added within 20 min at 46-48° C. another 350 ml water. The solution was cooled within 1 h to 20° C. and stirred for 2 h. The suspension formed was filtered, the crystals were washed twice with 50 ml water and dried under high vacuum for 18 h at 45° C. to yield 91.6 g (91.5%) of (S)-11-1 as white crystals.

EXAMPLE 1b

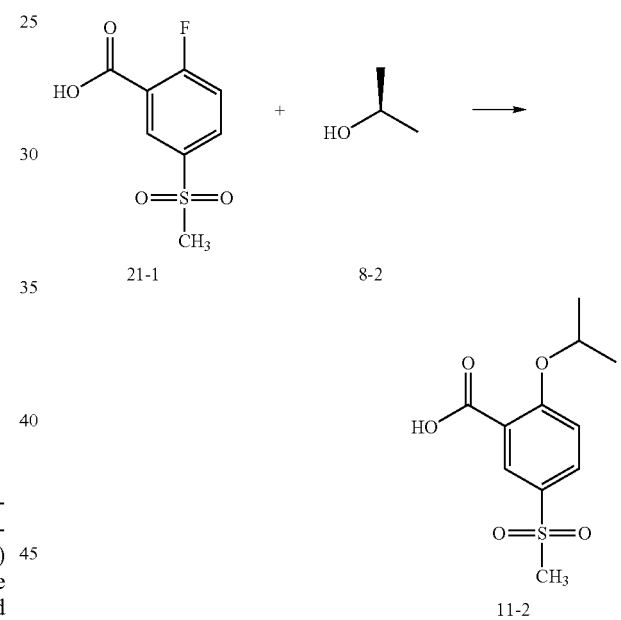

Equipment: 100 ml four-necked round bottom flask equipped with a temperature probe, a mechanical stirrer and an inert gas supply.

To a white suspension of 1.0 g 2-fluoro-5-methanesulfonyl-benzoic acid (21-1, 4.6 mmol) in 30 ml 2-propanol 8-2 was added 4.5 g cesium carbonate (13.8 mol). The white reaction suspension was warmed to 80° C. and stirred under argon for 67 h. The solvent of the reaction mixture was evaporated and the residue treated with 20 ml CH$_2$Cl$_2$ and 10 ml water. The pH of the water phase was adjusted to 1.5 by addition of ca. 14 ml 2N HCl. After extraction the phases were separated and the water phase extracted twice with 10 ml CH$_2$Cl$_2$. The combined organic phase was evaporated to get the crude product in quant. yield. Crystallization from EtOAc/hexane yielded 1.02 g 11-2 as white crystals in 87%. (HPLC analysis >98 area-%).

EXAMPLE 1c

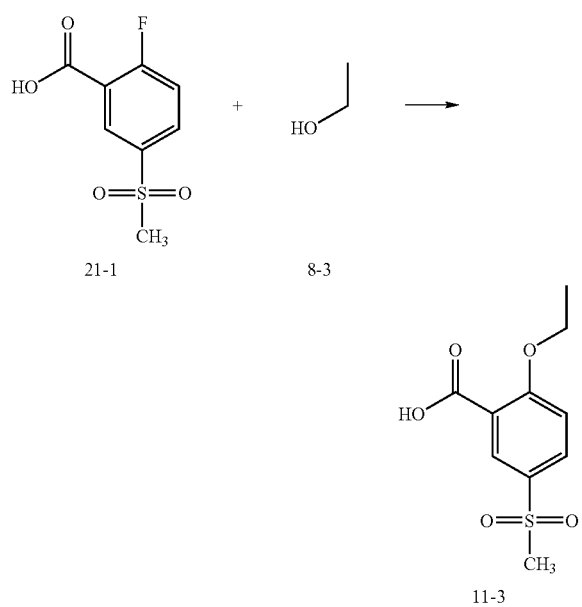

Equipment: 500 ml four-necked round bottom flask equipped with a temperature probe, a mechanical stirrer, a cooler and an inert gas supply.

To a white suspension of 15.1 g 2-fluoro-5-methanesulfonyl-benzoic acid (21-1, 69.2 mmol) in 302 ml ethanol 8-3 was added 68.3 g cesium carbonate (207.6 mol). The white reaction suspension was warmed to 80° C. and stirred under argon for 18 h. The solvent of the reaction mixture was evaporated and the residue treated with 150 ml EtOAc and 150 ml water. The pH of the water phase was adjusted to 1.5 by addition of ca. 75 ml HCl 25%. After extraction the phases were separated and the water phase extracted with 150 ml EtOAc. The combined organic phase was evaporated to a volume of 150 ml and treated with 150 ml heptane. The suspension formed was filtered, the crystals were washed with 150 ml EtOAc/heptane 1:1 and dried to yield 14.4 g 11-3 as white crystals in 85%. (HPLC analysis 99.7 area-%).

EXAMPLE 2

(S)-trifluoro-isopropanol ((S)-8-1)

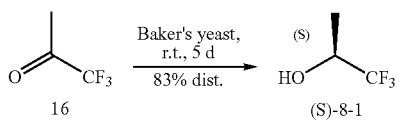

Equipment:

800 l vessel equipped with a temperature probe at the bottom of the vessel, a temperature probe dipping into the reaction mixture, a mechanical stirrer and an inert gas supply A brown suspension of 240 l phosphate buffer pH 7.5 and 240 kg Baker's yeast (Klipfel AG (Rheinfelden), Sackhefe 104020, stored at 4° C.) was stirred at room temperature for 1 h, heated up to 50° C. within 85 min and held at 50.3° C. (±0.5° C.) for 1.5 h. The pH of the suspension was maintained at 7.5 by addition of KOH (50%), with the aid of a pH-stat. The suspension was cooled to 10° C. within 120 min, diluted with 320 l phosphate buffer pH 7.5 and stirred for 24 h at 10° C. To the mixture was added within 100 min 24.7 kg trifluoroacetone (16, 220.4 mmol, pre-cooled to <10° C.). The reaction mixture was warmed to 20° C. and stirred for 159 h at this temperature (the pH of the suspension was maintained at 7.5 by addition of KOH (50%), with the aid of a pH-stat.

To the mixture was added 0.5 kg antifoam BC 86/013 (Basildon Chemical Company (England), antifoam BC 86/013, silicone/non-silicone based antifoam compound), heated to 60° C. and the product was distilled off at 140 mbar to yield 101 kg mixture of (S)-trifluoro-isopropanol (S)-8, water and ethanol. 101 kg mixture of (S)-trifluoro-isopropanol (S)-8, water and ethanol was distilled on a 50 l rotavap in 3 portions at 90° C. starting from 1013 mbar to 500 mbar. The combined fractions yielded 28.5 kg mixture of (S)-trifluoro-isopropanol (S)-8-1, water and ethanol. 28.5 kg (S)-trifluoro-isopropanol (S)-8-1 was distilled on a Sulzer-column (5×150 cm Sulzer packing BX) in 2 portions at 115° C. and 1013 mbar to yield (including redistilled side fractions) 21.8 kg (82.9%) of (S)-trifluoro-isopropanol ((S)-8-1).

GC analysis: 95.1 m/m-% of (S)-8-1 er=99.7:0.3

EXAMPLE 3

2,3-difluoro-5-trifluoromethylpyridine (12-2)

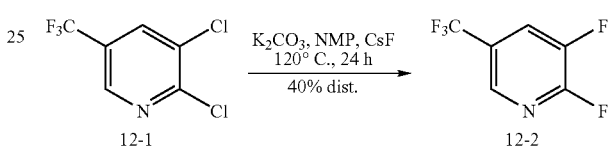

Equipment:

2.5 l four-necked round bottom flask equipped with a thermometer, a mechanical stirrer a dropping funnel and an inert gas supply 150 ml N-methyl-2-pyrrolidinone was evaporated at 110° C. and 25-30 mbar from a suspension of 2 l N-methyl-2-pyrrolidinone, 28 g potassium carbonate (202.6 mmol), and 615.0 g cesium fluoride (4.0 mol). The reaction mixture was treated with 170.0 g 2,3-dichloro-5-trifluoromethylpyridine (12-1, 779.2 mmol) and stirred at 120° C. for 24 h.

The product 12-2 was directly distilled out of the reaction suspension at 95 to 110° C. and 40-50 mbar yielding 190 g of 12-2 as a mixture. 190 g of this mixture were extracted with 200 ml pentane and 400 ml water. After separation of the phases, the water phase was extracted with 2 l pentane. The combined pentane phase was distilled on a Sulzer-column at 40 to 100° C. yielding 60.0 g (40.4%) of 12-2.

GC analysis: 99.9 area-% of 12-2

EXAMPLE 3b

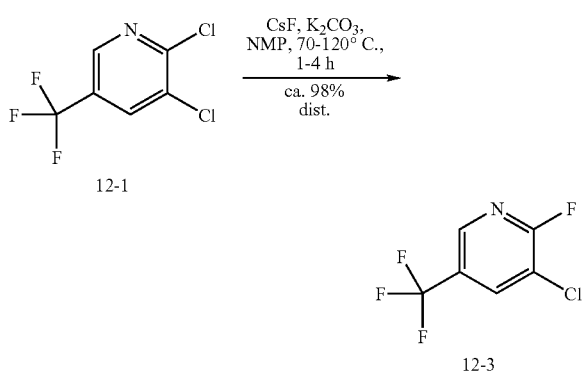

Equipment:

250 ml four-necked round bottom flask equipped with a thermometer, a mechanical stirrer a dropping funnel and an inert gas supply 25 ml DMSO was evaporated at 120° C. and 25-30 mbar from a suspension of 150 ml DMSO, 2.5 g potassium carbonate (17.9 mmol) and 25.0 g cesium fluoride (162.9 mmol). The reaction mixture was treated with 25.0 g 2,3-dichloro-5-trifluoromethylpyridine (12-1, 112.3 mmol) and stirred at 120° C. for 4 h. The suspension was filtered and the product 12-3 was directly distilled out of the distillate at 95 to 115° C. and 40-60 mbar to get 12-3 in quantitative yield. GC analysis: 96.9 area-% of 12-3.

EXAMPLE 4

Synthesis of 1-(3-fluoro-5-trifluoromethyl-pyridin-2-yl)-piperazine (15-1)

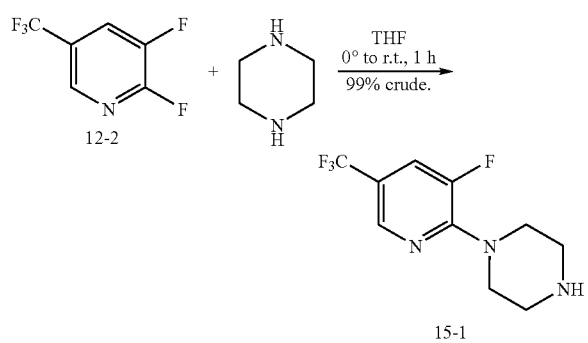

Equipment:

A suspension of 1.0 kg piperazine (12.1 mol) in 15.0 l THF was treated at 0° C. within 30 min with a solution of 732.0 g 2,3-difluoro-5-trifluoromethylpyridine 12-2, (4.0 mol) in 2.0 l THF. The reaction mixture was stirred for 30 min at 0° C. and heated to room temperature within 30 min.

The white reaction mixture was extracted with 15 l water and 15 l toluene. After separation of the phases the water phase was extracted with 10 l toluene. The combined organic phase was washed twice with 10 l in total with 20 l water. The solvent of the organic phase was evaporated at 45° C. and 50 mbar to yield 984.0 g (99.3%) of 15-1 as white solid.

GC analysis: 98.9 area-% of 15-1

EXAMPLE 5

Synthesis of [4-(3-fluoro-5-trifluoromethyl-pyridin-2-yl)-piperazin-1-yl]-[5-methanesulfonyl-2-(2,2,2-trifluoro-1-methyl-ethoxy)-phenyl]-methanone ((S)-1-1)

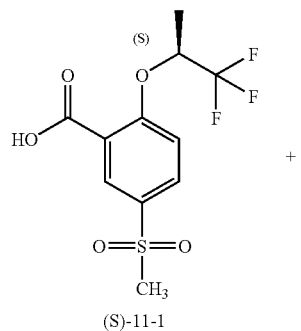

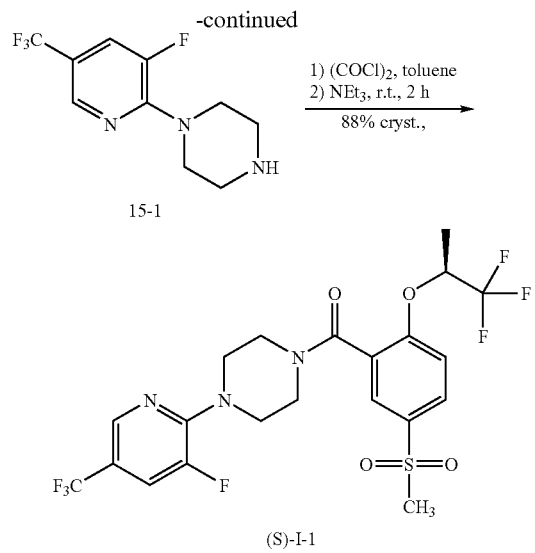

Equipment:

A suspension of 1.2 kg 5-methanesulfonyl-2-(2,2,2-trifluoro-1-methyl-ethoxy)-benzoic acid ((S)-11-1, 4.0 mol) and 50 ml DMF in 15 l toluene was treated at room temperature within 1 h with a solution of 485.2 g oxalyl chloride (3.7 mol) in 650 ml toluene. The suspension was stirred for 1 h at room temperature and dropped at room temperature within 30 to 45 min to a solution of 1.0 kg 1-(3-fluoro-5-trifluoromethyl-pyridin-2-yl)-piperazine (15-1, 4.0 mol) in 12 l toluene and 1.1 l triethylamine (7.9 mol). The reaction mixture was stirred at room temperature for 30 min.

The suspension was filtered and the residue washed in portions with 5 l toluene. The filtrate was extracted with 15 l water. After separation of the phases, the organic phase was washed with 15 l sodium bicarbonate 5% and 7 l NaCl solution 5%. The solvent of the organic phase was evaporated (50° C., 400 mbar) and treated with 20 l EtOH. The solution was hot filtrated and the solvent evaporated at 50° C. to a volume of ca. 10 l. The solution was heated to 60° C., treated within 30 min with 25 l heptane and cooled within 4 h to 20° C. The white suspension was stirred at this temperature over night, cooled to 0° C. and stirred for 1 h at 0° C. After filtration the crystals were washed in portions with a cooled mixture of 3 l EtOH and 7 l heptane to yield 1795 g (88.2%) of (S)-1-1 as white crystals.

HPLC analysis 99.8 area-% of (S)-1-1 er=99.4:0.6%

EXAMPLE 5b

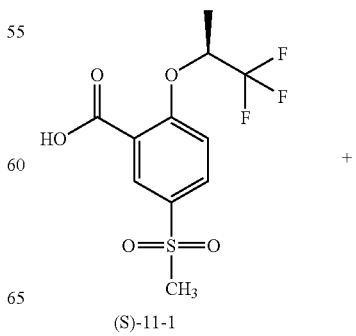

-continued

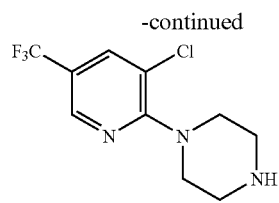

15-2

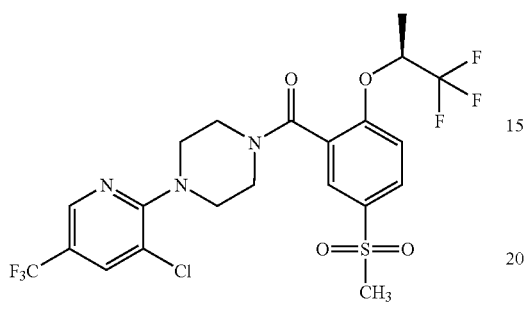

(S)-I-2

Equipment: 100 ml three-necked round bottom flask equipped with a thermometer, a mechanical stirrer and an inert gas supply A solution of 200 mg 5-methanesulfonyl-2-(2,2,2-trifluoro-1-methyl-ethoxy)-benzoic acid ((S)-11-1, 0.63 mmol) in 20 ml $CH_2Cl_2$ was treated at room temperature with 166 mg diisopropylethyl amine. To the mixture was added at 0° C. 70 mg ethyl chloroformate (0.63 mmol) and stirred for 60 min. The reaction mixture was treated with 166.8 mg 1-(3-chloro-5-trifluoromethyl-pyridin-2-yl)-piperazine (15-2, 0.63 mmol) and stirred for ca. 2 h. The mixture was warmed to room temperature and treated with 15 ml $CH_2Cl_2$ and 5 ml water. After extraction the phases were separated and the aqueous phase was extracted with 5 ml $CH_2Cl_2$. The combined organic phase was evaporated under reduced pressure to yield the crude product as an oil. After chromatographic purification 120 mg of (S)-1-2 was yielded (crystallization from hexane also works).

HPLC analysis 96.6 area-% of (S)-1-2

EXAMPLE 5c

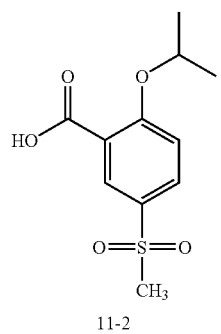

11-2

+

-continued

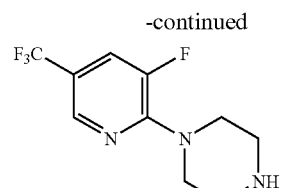

15-1

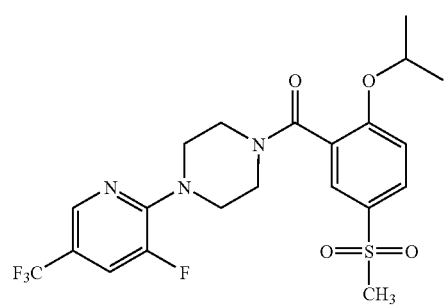

I-3

Equipment:

100 ml four-necked round bottom flask equipped with a thermometer, a mechanical stirrer and an inert gas supply A solution of 200 mg of 2-isopropoxy-5-methanesulfonyl-benzoic acid (11-2, 0.77 mmol) in 20 ml $CH_2Cl_2$ was treated at room temperature with 214.4 mg diisopropylethyl amine (1.63 mmol). The reaction mixture was cooled to −5° C., treated with 85.7 mg ethyl chloroformate (0.77 mmol) and stirred for 60 min at this temperature. A solution of 221.1 mg 1-(3-fluoro-5-trifluoromethyl-pyridin-2-yl)-piperazine (15-1, 0.77 mmol) and 102.1 mg diisopropylethyl amine (0.77 mmol) in 10 ml $CH_2Cl_2$ was added at −5° C. The reaction mixture was stirred for 4 h warmed to room temperature and treated with 15 ml water. After extraction the phases were separated and the aqueous phase was extracted twice with 5 ml $CH_2Cl_2$. The combined organic phase was evaporated under reduced pressure to yield the crude product as an oil. After chromatographic purification 40 mg of 1-3 was yielded.

HPLC analysis 96.6 area-% of (S)-1-3

EXAMPLE 5d

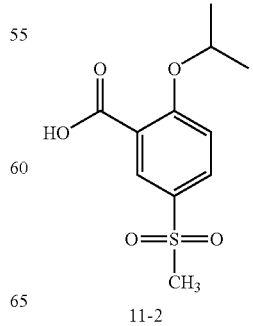

11-2

+

-continued

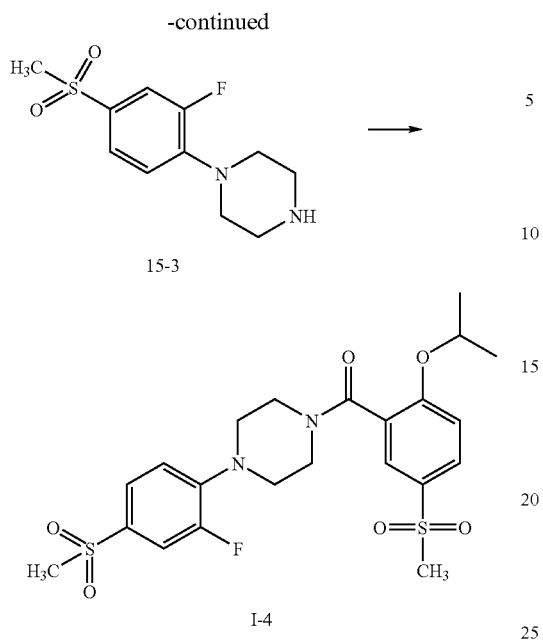

-continued

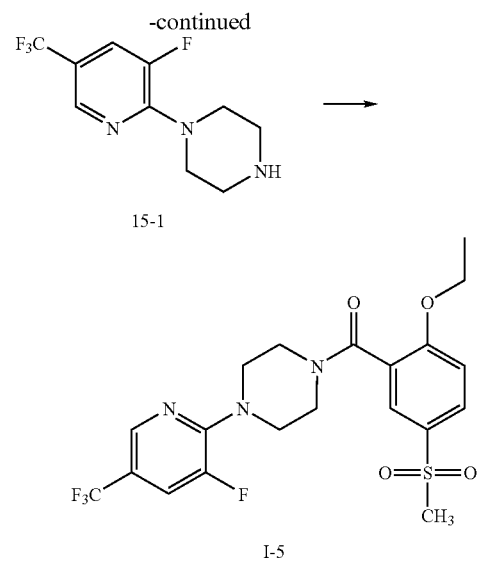

Equipment:

250 ml four-necked round bottom flask equipped with a thermometer, a mechanical stirrer and an inert gas supply A solution of 5.0 g of 2-isopropoxy-5-methanesulfonyl-benzoic acid (11-2, 19.4 mmol) in 150 ml $CH_2Cl_2$ was treated at room temperature with 2.8 g diisopropylethyl amine (21.3 mmol). The reaction mixture was cooled to 0° C., treated with a solution of 2.1 g ethyl chloroformate (19.4 mmol) in 50 ml $CH_2Cl_2$ and stirred for 2 h at this temperature. A solution of 5.1 g 1-(4-methanesulfonyl-2-fluoro-phenyl)-piperazine (15-3, 19.36 mmol) in 50 ml $CH_2Cl_2$ was added at 0° C. within 15 min. The reaction mixture was stirred for 2 h warmed to room temperature and treated with 15 ml water. After extraction the phases were separated and the aqueous phase was extracted twice with 10 ml $CH_2Cl_2$. The combined organic phase was evaporated under reduced pressure to yield the crude product as an oil. Crystallization from EtOAc yielded 6.25 g of I-4 as white powder.

HPLC analysis 96.6 area-% of I-4.

EXAMPLE 5e

Equipment:

350 ml four-necked round bottom flask equipped with a thermometer, a mechanical stirrer and an inert gas supply A suspension of 11.0 g of 2-ethoxy-5-methanesulfonyl-benzoic acid (11-3, 19.4 mmol) in 110 ml toluene was treated at room temperature with 0.5 ml DMF. The reaction mixture was treated with a solution of 3.7 ml oxaly chloride (42.7 mmol) in 10 ml toluene. The suspension was stirred for 1 h at room temperature and dropped to a solution of 11.3 g 1-(3-fluoro-5-trifluoromethyl-pyridin-2-yl)-piperazine (15-1, 44.8 mmol) and 12.0 ml triethyl amine (85.8 mmol) in 140 ml toluene. The suspension was stirred for 30 min at room temperature, filtered and the residue rinsed with 100 ml toluene. The filtrate was washed three times with 400 ml water. The solvent of the organic phase was evaporated and the residue treated with 250 ml EtOH. Ca. 150 ml EtOH were evaporated at 60° C. and 300 ml heptane added within 30 min. The mixture was cooled to room temperature within 4 h, the formed suspension cooled to 0° C. and stirred for 1 h. The crystals were filtered, washed with 120 ml EtOH/heptane 1:2 and dried for 24 h at 50° C. to yield 16.5 g (81.3%) product I-5 as white crystals.

HPLC analysis 99.8 area-% of I-5

The invention claimed is:

1. A process of making a compound of formula (S)-I-1

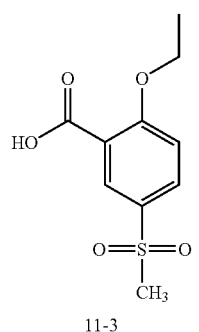

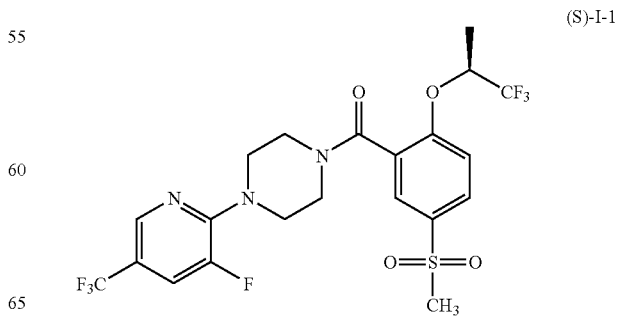

comprising
a) reacting a compound of formula

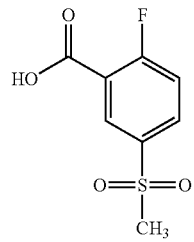
21-1 with a compound of formula

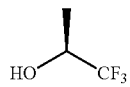

(S)-8-1 to obtain a compound of formula

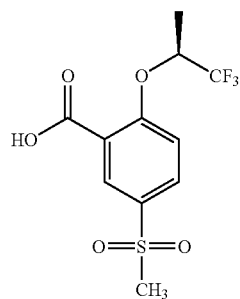
(S)-11-1 and
b) coupling the compound of formula (S)-11-1 in the presence of a coupling reagent or the corresponding acid halogenide with a compound of formula

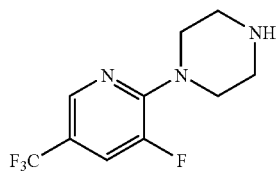
15-1 to obtain the compound of formula

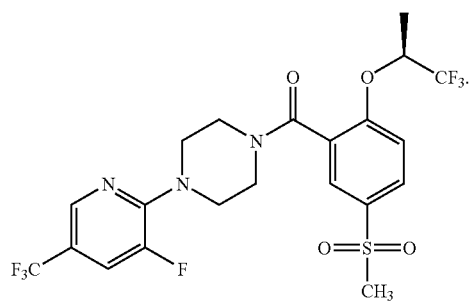
(S)-I-1

2. The process of claim 1, wherein step a) is carried out in an autoclave in the presence of N,N-dimethyl-acetamide and cesium carbonate at a temperature of 100 -150 ° C. at 1.5 bar for 16 -80 hours or with KOtBu in THF at room temperature.

3. The process of claim 1, wherein step b) is carried out in toluene, DMF, THF or $CH_2Cl_2$ at room temperature within 1 hour in the presence of oxalyl chloride, thionyl chloride, ethyl chloroformate, TBTU, HBTU, CDI or EDCI.

4. The process of claim 1, wherein the compound of formula 15-1 is prepared by the process comprising a) reacting a compound of formula

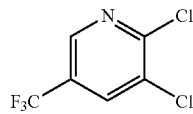
12-1 with CsF and $K_2CO_3$ or any other base in NMP, DMSO or other solvents with high boiling points to the compound of formula

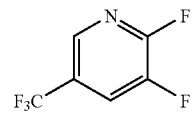
12-2 and then
b) with piperazine in THF or toluene to the corresponding compound of formula

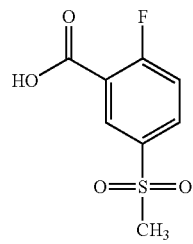
15-1

5. The process of claim 1, wherein the compound of formula (S)-8-1 is prepared by the process comprising reacting a compound of formula $CH_3C(O)CF_3$ with Baker's yeast or with Ru-catalysts.

6. The process of claim 1, wherein the compound of formula 21-1

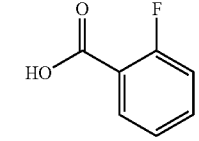
21-1 is prepared by the process comprising reacting a compound of formula 17

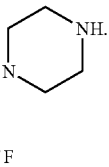
17 with chlorosulfuric acid to produce a compound of formula 20

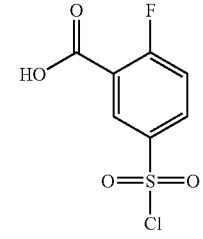
20 and then reacting a compound of 20 with sodium sulfite and $ClCH_2CO_2H$.

* * * * *